(12) United States Patent
Stopp

(10) Patent No.: US 11,928,828 B2
(45) Date of Patent: Mar. 12, 2024

(54) DEFORMITY-WEIGHTED REGISTRATION OF MEDICAL IMAGES

(71) Applicant: Brainlab AG, Munich (DE)

(72) Inventor: Sebastian Stopp, Munich (DE)

(73) Assignee: BRAINLAB AG, Munich (DE)

( * ) Notice: Subject to any disclaimer, the term of this patent is extended or adjusted under 35 U.S.C. 154(b) by 359 days.

(21) Appl. No.: 17/603,280

(22) PCT Filed: May 28, 2019

(86) PCT No.: PCT/EP2019/063719
§ 371 (c)(1),
(2) Date: Oct. 12, 2021

(87) PCT Pub. No.: WO2020/239200
PCT Pub. Date: Dec. 3, 2020

(65) Prior Publication Data
US 2022/0189045 A1    Jun. 16, 2022

(51) Int. Cl.
*G06T 7/33* (2017.01)
*A61B 34/10* (2016.01)

(52) U.S. Cl.
CPC .............. *G06T 7/337* (2017.01); *A61B 34/10* (2016.02); *A61B 2034/105* (2016.02);
(Continued)

(58) Field of Classification Search
CPC .............. A61B 2034/105; A61B 34/10; G06T 2207/10081; G06T 2207/10088;
(Continued)

(56) References Cited

U.S. PATENT DOCUMENTS

2014/0044333 A1   2/2014   Barth, Jr. et al.
2015/0189378 A1*  7/2015   Soundararajan ............................
                                                                    H04N 21/44231
                                                                    725/12
(Continued)

FOREIGN PATENT DOCUMENTS

WO      2020239200      12/2020

OTHER PUBLICATIONS

International Search Report and Written Opinion for Application No. PCT/EP2019/063719 dated Jul. 31, 2019. 11 pages.
(Continued)

*Primary Examiner* — Ajibola A Akinyemi
(74) *Attorney, Agent, or Firm* — Gray Ice Higdon

(57) ABSTRACT

Disclosed is a computer-implemented method of determining a spatial relationship between planning image data and current surface data which leads to improved surface registration accuracy by considering the elasticity and deformability of the tissue. The knowledge about the tissue can be estimated based on type of tissue and atlas information. For the process of generating surface registration points on specific anatomical regions, e.g. the face or forehead, are acquired with a classical navigated pointer or laser pointer. It is also possible to acquire points with surface scanners. Confidence values defining a probability for certain parts of the surface registration points being deformed in comparison to a planning image are read from atlas data and used to compensate for the deformation in the registration between the surface registration points and the planning image in order to render the registration valid.

13 Claims, 2 Drawing Sheets

(52) U.S. Cl.
CPC .............. *G06T 2207/10081* (2013.01); *G06T 2207/10088* (2013.01); *G06T 2207/30004* (2013.01)

(58) Field of Classification Search
CPC ....... G06T 2207/30; G06T 2207/30004; G06T 7/337; G06T 7/35
USPC ........................................................ 382/128
See application file for complete search history.

(56) References Cited

U.S. PATENT DOCUMENTS

| 2017/0143430 | A1 | 5/2017 | Miga | |
| 2017/0231501 | A1* | 8/2017 | Culver | A61B 5/0042 600/425 |
| 2018/0235714 | A1* | 8/2018 | Kuo | A61B 5/706 |

OTHER PUBLICATIONS

Sun Kay et al., "Near Real-Time Computer Assisted Surgery for Brain Shift Correction Using Biomechanical Models" IEEE Journal of Translational Engineering in Health and Medicine. vol. 2, May 30, 2014. pp. 1-13. XP011552671, DOI: 10.1109/JTEHM.2014.2327628.

Pallone et al., "Combining supine MRI and 3D optical scanning for improved surgical planning of breast conserving surgeries" Proceedings SPIE 7513, 2009 International Conference on Optical Instruments and Technology. vol. 8316. p. 83163B, XP009514560. ISSN: 0277-786X, DOI: 10.1117/12.912803 ISBN: 978-1-5106-2781-9. Retrieved from the Internet: URL:http://proceedings.spiedigitallibrary.org/proceeding.aspx?doi=10.1117/12.912803.

Eiben et al., "Surface driven bimechanical breast image registration" Progress in Biomedical Optics and Imaging SPIE International Society for Optical Engineering. vol. 9786, Mar. 18, 2016. pp. 97860W-97860W, XP060069322, ISSN: 1605-7422, DOI: 10.1117/12.2216728. ISBN: 978-1-5106-0027-0.

Krell et al., "Assessment of Iterative Closest Point Registration Accuracy for Different Phantom Surfaces Captured by an Optical 3D Sensor in Radiotherapy" Computational and Mathematical Methods in Medicine. Retrieved from https://www.ncbi.nlm.nih.gov/pmc/articles/PMC5253513.

Marmulla et al., "Physiological shift of facial skin and its influence on the change in precision of computer-assisted surgery" British Journal of Oral and Maxillofacial Surgery. 44 (2006) 273-278.

* cited by examiner

DEFORMITY-WEIGHTED REGISTRATION OF MEDICAL IMAGES

FIELD OF THE INVENTION

The present invention relates to a computer-implemented method of determining a spatial relationship between planning image data and current surface data, a corresponding computer program, a program storage medium storing such a program and a computer for executing the program, as well as a medical system comprising an electronic data storage device and the aforementioned computer.

TECHNICAL BACKGROUND

It is known from literature that the anatomical surface of patients changes between pre-operative imaging (CT, MRT) and intraoperative registration of the patient's position (determined by a surface scan or using a tracked pointing device). So, even a perfectly measured preoperative and intraoperative surface point cloud lead to an error prone registration. Due to anatomical differences in the used regions, the deviation between pre and intra op is distributed in a patchy manner, e.g. the deformation (also called swelling) is not homogeneous: While for example the deviation on the forehead region is relatively small, the error on softer tissue regions (e.g. cheeks) is larger.

The present invention has the object of providing an improved method of registering a patient's current position with a planning image.

The present invention can be used for registration procedures e.g. in connection with a system for surface registration such as z-Touch® and a system for image-guided radiotherapy such as ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention is concerned with improving surface registration accuracy by considering the elasticity and deformability of the tissue (potential swellings). The knowledge about the tissue can be estimated based on type of tissue and atlas information. For the process of generating surface registration points on specific anatomical regions, e.g. the face or forehead, are acquired with a classical navigated (i.e. tracked) pointer or laser pointer. It is also possible to acquire points with surface scanners (e.g. structured light, 3D camera, time-of-flight). Confidence values defining a probability for certain parts of the surface registration points being deformed in comparison to a planning image are read from atlas data and used to compensate for the deformation in the registration between the surface registration points and the planning image in order to render the registration valid.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining a spatial relationship between planning image data and current surface data. The method comprises executing, on at least one processor of at least one computer (for example at least one computer being part of the navigation system), the following exemplary steps which are executed by the at least one processor.

In a (for example first) exemplary step, planning image data is acquired which describes a three-dimensional medical image of an anatomical body part having an external surface (for example, a surface which does not directly neighbour and/or touch any other anatomical structure, i.e. and outer surface). For example, the planning image data has been generated by applying magnetic resonance tomography imaging or computed x-ray tomography imaging to the anatomical body part.

In a (for example second) exemplary step, current surface data is acquired which describes a current surface scan describing the external surface. The current surface scan is defined for example by a point cloud, i.e. a set of points defined in three-dimensional space which define the positions at which the surface has been scanned. For example, the current surface data has been generated by using a tracked pointing instrument to acquire positional information describing the position of the external surface. Alternatively, the current surface data has been generated by applying a surface scanning imaging modality including use of a surface acquiring device such as at least one of a range camera, thermographic camera, structured light camera or time-of-flight camera.

In a (for example third) exemplary step, atlas data is acquired which describes a model of the external surface and confidence values for elements of the external surface which describe a probability for the geometry of the external surface to be subject to a change (also called deformation or swelling), for example compared to a standard situation such as the one in which for example the planning image data was generated. The model is for example image-based, i.e. generated from a plurality of medical images taken from for example different patients and for example conducting a statistical analysis of those images, or object-based, i.e. generated from one or more synthetically generated digital objects (which have been produced for example by manual user interaction such as using a drawing program or by otherwise, e.g. numerically, defining the geometry of the objects) which are meant to resemble human anatomy, namely the external surface. The confidence values are for example represented by numeric values. In an example, the atlas data describes a direction and for example a distance in which the elements (i.e. constituents) of the external surface move when the geometry of the external surface is subject to the change. For example, the change (for example, deformation) is due to at least one of positioning the patient, gravity, swelling of tissue included in the external surface, or elastic deformation of tissue included in the external surface. For example, the probability depends on whether the geometry of the external surface is at least substantially defined by the hardness of tissue included in or lying closely below the external surface. In other words, the probability depends for example on the elasticity (for example, hardness) of tissue included in or lying closely below the external surface. Limiting the probability to this region of tissue avoids consideration of hard tissue such bony tissue and/or cartilage which generally does not deform due to the aforementioned causes for the change. For example, the probability is higher the lower the hardness of the tissue included in or lying closely below the external surface. In other words, the probability for example increases with decreasing hardness of the tissue lying in or closely below the external surface. For example, the confidence values depend on the time interval lying in between the point in in time at which the registration data has been determined and the point in time at which the anatomical body part will be re-positioned. Alternatively, the confidence values depend on for example the imaging modality used to generate the current surface data. For example, the confidence values have been determined by at least one of the following three possibilities a) to c):

a) determining a typical deformation of the external surface determined from a plurality of comparisons of planning image data with current surface data acquired for example for different patients;

b) using pre-defined confidence values derived from expert knowledge as the confidence values;

c) using a physical property (for example, the value of at least one elastic variable such as the shear modulus or the bulk modulus) of tissue included in or lying closely below the external surface as a basis for computing the confidence values.

In a (for example fourth) exemplary step, confidence assignment data is determined based on the atlas data and the current surface data, wherein the confidence assignment data describes an assignment of the confidence values for elements of the external surface described by the atlas data to the corresponding elements of the external surface described by the current surface scan. For example, the confidence assignment data is determined by determining preliminary confidence assignment data based on the atlas data and the planning image data, wherein the preliminary confidence assignment data describes an assignment of the confidence values for elements of the external surface described by the atlas data to the corresponding elements of the external surface described by the medical image described by the planning image data. The assignment of the confidence values for elements of the external surface described by the atlas data to the corresponding elements of the external surface described by the medical image described by the planning image data is for example done by registering the atlas data and the patient image data by executing an image fusion algorithm on the two data sets to establish a spatial relationship between the reference system in which positions in the atlas data are defined and the reference system in which positions in the planning image data are defined, and the assigning the confidence values from the atlas data to anatomical structures depicted in the medical image described by the planning image data which correspond to anatomical structures to which the confidence values are assigned (i.e. with which they are associated) in the atlas data. Alternatively, a surface is for example interpolated between the points described by the current surface data, and those surface are fused (i.e. registered) to the atlas data by executing an image fusion algorithm, and the confidence values assigned to corresponding surfaces in the atlas data are assigned to the respective point described by the current surface data. The registration data is then determined by establishing the spatial relationship (e.g. mapping) between the external surface described by the planning image data and the external surface described by the current surface data (for example as described below with regard to the for example fifth exemplary step) and applying (for example, assigning) the confidence values to the spatial relationship for the respective element of the external surface to which the confidence value is assigned and for which the spatial relationship has been or is being established. Thereby, the spatial relationship is weighted for that element by the confidence value assigned to that element. In one example, the atlas data is first registered to the planning image data, and then the assignment of the confidence values to individual image elements (e.g. voxels or pixels) is transferred to the registration for the respective image element between the medical image described by the planning image data and the current surface scan.

In a (for example fifth) exemplary step, registration data is determined based on the planning image data and the current surface data and the confidence assignment data, wherein the registration data describes a spatial relationship (for example, a metric or distance, embodied by for example a mapping) between the external surface described by the planning image data and the external surface described by the current surface data, wherein the spatial relationship is weighted for the elements of the external surface according to the confidence value assigned to the respective element. For example, the spatial relationship between the external surface described by the planning image data and the external surface described by the current surface data is determined by computing a norm between each point defining the current surface scan and the external surface described by the planning image data, or by applying an iterative closest point algorithm to the planning image data and the current surface data. If the atlas data describes a direction and for example a distance in which the elements (i.e. constituents) of the external surface move when the geometry of the external surface is subject to the change, the spatial relationship is determined for example by compensating for that movement, i.e. determining the spatial relationship includes compensating for that movement.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore alternatively or additionally relates to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
a) the at least one computer according to the fourth aspect;
b) at least one electronic data storage device storing at least the planning surface data and the atlas data; and
c) a surface acquiring device (for example, at least one of a range camera, thermographic camera, structured light camera or time-of-flight camera) for acquiring the current surface data,
  wherein the at least one computer is operably coupled to
  the at least one electronic data storage device (3) for acquiring, from the at least one data storage device, at least the planning image data and the atlas data, and
  the surface acquiring device for acquiring, from the surface acquiring device, the current surface data.

Alternatively or additionally, the invention according to the fifth aspect is directed to a for example non-transitory computer-readable program storage medium storing a program for causing the computer according to the fourth aspect to execute the data processing steps of the method according to the first aspect.

In a sixth aspect, the present invention relates to the use of the system according to the fifth aspect for registering an external surface of an anatomical body part with planning image data describing the anatomical body part.

In a seventh aspect, the invention relates to an atlas data set (i.e. an electronic atlas data set) describing an image-based model of an external surface and confidence values for elements of the external surface which describe a probability for the geometry of the external surface to be subject to a change.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received, read or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data.

The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc.

Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
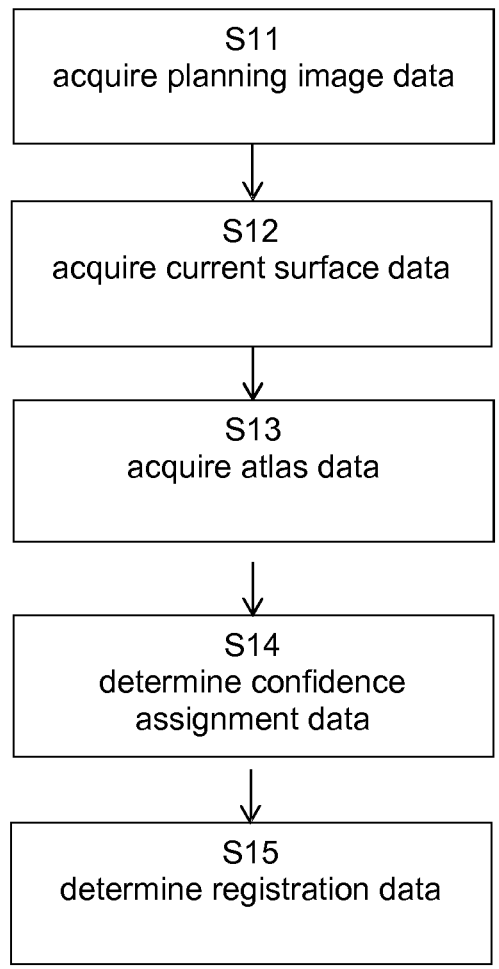
FIG. 1 illustrates the basic flow of the method according to the first aspect.
Figure 2:
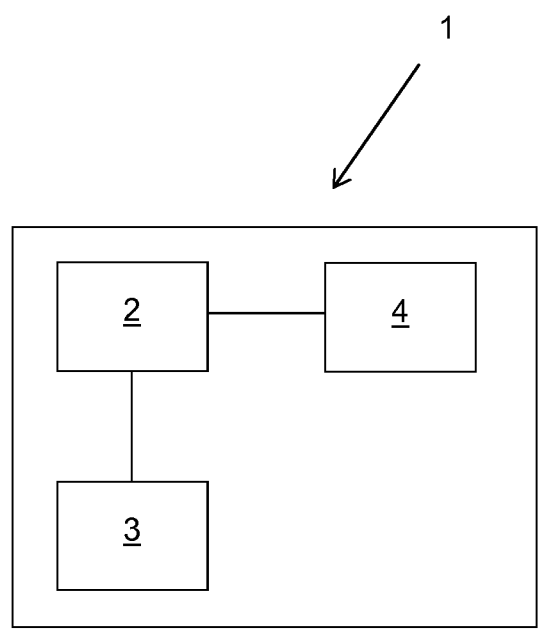
FIG. 2 is a schematic illustration of the system according to the fifth aspect.

FIG. 1 illustrates the basic steps of the method according to the first aspect, in which step S11 encompasses acquisition of the planning image data, step S12 encompasses acquisition of the current surface data and subsequent step S13 encompasses acquisition of the atlas data. These data sets serve as input to the subsequent steps S14 of determining the confidence assignment data and S15 of determining the registration data.

The disclosed method uses anatomical knowledge for point accuracy estimation weighting. Points acquired on harder regions get higher confidence than points on softer regions. During a surface registration of a face, the swelling of the soft tissue areas (e.g. the cheeks) can lead to a tilted registration. This can be reduced or even avoided with the weighting of points with a confidence value for a specific region. Additionally the number of points versus confidence value need to be considered:
A single point acquired on the front teeth can be more accurate than 20 points on a potentially swollen cheek.

This disclosure therefore proposes a multi-step registration:
1. Rough pre-registration in the following two steps:
   a. The surface of the anatomical structure is scanned
   b. The surface is registered to a preoperative three-dimensional scan
2. Using atlas information for anatomical area confidence value point weighting in the following three steps:
   a. The surface is registered to atlas information.
   b. In the atlas, the body regions are labelled with confidence values which define how elastic the tissue is, how sensitive the region is to swelling, how sensitive the region is to tissue shifting etc.
   c. The atlas confidence values are transferred to the 3D surface point cloud.
3. The registration is adjusted by the following two steps:
   a. According to the added confidence values, every point on the surface is weighted.
   b. The registration is adapted based on the weighted point cloud.

FIG. 6 is a schematic illustration of the medical system 1 according to the fifth aspect. The system is in its entirety identified by reference sign 1 and comprises a computer 2, an electronic data storage device (such as a hard disc) 3 for storing at least the patient data and a surface detecting device 4. The components of the medical system 1 have the functionalities and properties explained above with regard to the fifth aspect of this disclosure.

The invention claimed is:

1. A computer-implemented medical method of determining a spatial relationship between planning image data and current surface data, the method comprising the following steps:
   acquiring planning image data which describes a three-dimensional medical image of an anatomical body part having an external surface;
   acquiring current surface data which describes a current surface scan describing the external surface;
   acquiring atlas data which describes a model of the external surface and confidence values for elements of the external surface which describe a probability for the geometry of the external surface to be subject to a change;
   determining confidence assignment data based on the atlas data and the current surface data, wherein the confidence assignment data describes an assignment of the confidence values for elements of the external surface described by the atlas data to the corresponding elements of the external surface described by the current surface scan;
   determining registration data based on the planning image data and the current surface data and the confidence assignment data;
   wherein the registration data describes a spatial relationship between the external surface described by the planning image data and the external surface described by the current surface data; and further
   wherein the spatial relationship is weighted for the elements of the external surface according to the confidence value assigned to the respective element.

2. The method according to claim 1, wherein the change is due to at least one of positioning a patient, gravity, swelling of tissue included in the external surface, or elastic deformation of tissue included in the external surface.

3. The method according to claim 1, wherein the probability depends on whether the geometry of the external surface is at least substantially defined by the hardness of tissue included in or lying closely below the external surface.

4. The method according to claim 3, wherein the probability is higher the lower the hardness of the tissue included in or lying closely below the external surface.

5. The method according to claim 1, wherein:
   the confidence values depend on a time interval lying in between a point in time at which the registration data has been determined and the point in time at which the anatomical body part will be re-positioned, or
   the confidence values depend on an imaging modality used to generate the current surface data.

6. The method according to claim 1, wherein the confidence values have been determined by at least one of the following:
   determining a typical deformation of the external surface determined from a plurality of comparisons of planning image data with current surface data acquired for different patients;
   using pre-defined confidence values derived from expert knowledge as the confidence values; and
   using a physical property of tissue included in or lying closely below the external surface as a basis for computing the confidence values.

7. The method according to claim 1, wherein the confidence assignment data is determined by:
   determining preliminary confidence assignment data based on the atlas data and the planning image data;
   wherein the preliminary confidence assignment data describes an assignment of the confidence values for elements of the external surface described by the atlas data to the corresponding elements of the external surface described by the current surface scan; and
   wherein the registration data is determined by:
      establishing the spatial relationship between the external surface described by the planning image data and the external surface described by the current surface data; and
      applying the confidence values to the spatial relationship for the respective element of the external surface to which the confidence value is assigned and for which the spatial relationship has been or is being established, whereby the spatial relationship is weighted for that element by the confidence value assigned to that element.

8. The method according to claim 1, wherein the atlas data describes a direction and a distance in which the elements of the external surface move when the geometry of the external surface is subject to the change, and wherein the spatial relationship is determined by compensating for that movement.

9. The method according to claim 1, wherein the spatial relationship between the external surface described by the planning image data and the external surface described by the current surface data is determined by computing a norm between each point defining the current surface scan and the external surface described by the planning image data, or by applying an iterative closest point algorithm to the planning image data and the current surface data.

10. The method according to claim 1, wherein the planning image data has been generated by applying magnetic resonance tomography imaging or computed x-ray tomography imaging to the anatomical body part.

11. The method according to claim 1, wherein the current surface data has been generated by
   acquiring positional information using a tracked pointing instrument to describing the position of the external surface, or
   applying a surface scanning imaging modality including use of at least one of a range camera, thermographic camera, structured light camera or time-of-flight camera.

12. A computer implemented method which, when running on at least one processor on at least one computer, causes the at least one processor to:
   acquire planning image data which describes a three-dimensional medical image of an anatomical body part having an external surface;
   acquire current surface data which describes a current surface scan describing the external surface;
   acquire atlas data which describes a model of the external surface and confidence values for elements of the external surface which describe a probability for the geometry of the external surface to be subject to a change;
   determine confidence assignment data based on the atlas data and the current surface data, wherein the confidence assignment data describes an assignment of the confidence values for elements of the external surface described by the atlas data to the corresponding elements of the external surface described by the current surface scan;
   determine registration data based on the planning image data and the current surface data and the confidence assignment data;
   wherein the registration data describes a spatial relationship between the external surface described by the planning image data and the external surface described by the current surface data; and further
   wherein the spatial relationship is weighted for the elements of the external surface according to the confidence value assigned to the respective element.

13. A medical system, comprising:
   at least one processor on at least one computer which when executing instructions, causes the at least one processor to:
      acquire planning image data which describes a three-dimensional medical image of an anatomical body part having an external surface;
      acquire current surface data which describes a current surface scan describing the external surface;
      acquire atlas data which describes a model of the external surface and confidence values for elements of the external surface which describe a probability for the geometry of the external surface to be subject to a change;
      determine confidence assignment data based on the atlas data and the current surface data, wherein the confidence assignment data describes an assignment of the confidence values for elements of the external surface described by the atlas data to the corresponding elements of the external surface described by the current surface scan;
      determine registration data based on the planning image data and the current surface data and the confidence assignment data;
      wherein the registration data describes a spatial relationship between the external surface described by the planning image data and the external surface described by the current surface data; and further
      wherein the spatial relationship is weighted for the elements of the external surface according to the confidence value assigned to the respective element;
   at least one electronic data storage device storing at least planning surface data and atlas data; and
   a surface acquiring device for acquiring the current surface data,
   wherein the at least one computer is operably coupled to:
      the at least one electronic data storage device for acquiring, from the at least one electronic data storage device, at least the planning image data and the atlas data; and
      the surface acquiring device for acquiring, from the surface acquiring device, the current surface data.

* * * * *